(12) United States Patent
Kanner et al.

(10) Patent No.: US 10,441,401 B2
(45) Date of Patent: Oct. 15, 2019

(54) INCONTINENCE DEVICE

(71) Applicant: Rinovum Subsidiary 2, LLC, Monroeville, PA (US)

(72) Inventors: Glenn T. Kanner, Duxbury, MA (US); Stephen Bollinger, Export, PA (US)

(73) Assignee: RINOVUM SUBSIDIARY 2, LLC, Monroeville, PA (US)

( * ) Notice: Subject to any disclaimer, the term of this patent is extended or adjusted under 35 U.S.C. 154(b) by 76 days.

(21) Appl. No.: 15/657,555

(22) Filed: Jul. 24, 2017

(65) Prior Publication Data

US 2018/0021120 A1    Jan. 25, 2018

Related U.S. Application Data

(60) Provisional application No. 62/366,468, filed on Jul. 25, 2016.

(51) Int. Cl.
*A61F 2/00*    (2006.01)

(52) U.S. Cl.
CPC ............ *A61F 2/005* (2013.01); *A61F 2/0036* (2013.01); *A61F 2/0031* (2013.01); *A61F 2230/0052* (2013.01); *A61F 2250/0036* (2013.01)

(58) Field of Classification Search
CPC .................. A61F 2/0031; A61F 2/0036; A61F 2250/0036; A61F 2230/0052; A61F 2/005
USPC .............................................. 600/29–32, 37
See application file for complete search history.

(56) References Cited

U.S. PATENT DOCUMENTS

| 3,196,873 | A | | 7/1965 | Bletzinger et al. |
| 4,536,178 | A | | 8/1985 | Lichstein et al. |
| 4,726,805 | A | | 2/1988 | Sanders, III |
| 4,846,819 | A | | 7/1989 | Welch |
| 5,036,867 | A | * | 8/1991 | Biswas .................. A61F 2/005 128/885 |
| 5,256,133 | A | | 10/1993 | Spitz |
| 5,437,628 | A | | 8/1995 | Fox et al. |
| 5,603,685 | A | * | 2/1997 | Tutrone, Jr. ............ A61F 2/005 128/836 |
| 5,618,256 | A | * | 4/1997 | Reimer .................. A61F 2/005 128/DIG. 25 |
| 5,671,755 | A | | 9/1997 | Simon et al. |
| 5,771,899 | A | | 6/1998 | Martelly et al. |
| 5,785,640 | A | | 7/1998 | Kresch et al. |

(Continued)

*Primary Examiner* — Navin Natnithithadha
*Assistant Examiner* — Sunita Reddy
(74) *Attorney, Agent, or Firm* — Welsh Flaxman & Gitler LLC

(57) ABSTRACT

An incontinence device is insertable into and removable from a vaginal canal of a human user to apply pressure upon a urethra. The incontinence device includes a distal body member having a central core, a first arcuate arm on a first side of the central core and a second arcuate arm on a second opposite side of the central core. The first and second arcuate arms flex inward toward the central core into a first compressed position during insertion and expand outward away from the central core into a second in use position to fill the space in the middle and superior thirds of the vaginal canal in order to retain the incontinence device in the vaginal canal. The incontinence device also includes a proximal pressure member extending from the body member for resilient movement relative to the body member; wherein the pressure member applies pressure to support the urethra for controlling incontinence.

18 Claims, 8 Drawing Sheets

(56) References Cited

U.S. PATENT DOCUMENTS

| | | |
|---|---|---|
| 6,090,098 A | 7/2000 | Zunker et al. |
| 6,142,928 A | 11/2000 | Zunker et al. |
| 6,413,206 B2 | 7/2002 | Biswas |
| 6,418,930 B1 | 7/2002 | Fowler |
| 6,460,542 B1 * | 10/2002 | James ............. A61F 2/005 128/885 |
| 6,645,136 B1 | 11/2003 | Zunker et al. |
| 6,645,137 B2 | 11/2003 | Ulmsten et al. |
| 6,652,477 B2 | 11/2003 | Karapasha et al. |
| 6,676,594 B1 | 1/2004 | Zunker et al. |
| 6,695,763 B2 | 2/2004 | Zunker et al. |
| 6,739,340 B1 * | 5/2004 | Jensen ............. A61F 2/005 128/885 |
| 6,808,485 B2 | 10/2004 | Zunker |
| 6,939,289 B2 | 9/2005 | Zunker et al. |
| 7,263,999 B2 | 9/2007 | Kaseki et al. |
| 7,351,195 B2 | 4/2008 | Farrell |
| 7,628,156 B2 | 12/2009 | Astani et al. |
| 7,717,892 B2 | 5/2010 | Bartning et al. |
| 7,736,298 B2 | 6/2010 | Guerquin et al. |
| 7,771,344 B2 | 8/2010 | Ziv |
| 7,892,163 B2 | 2/2011 | Bartning et al. |
| 7,935,098 B2 | 5/2011 | Bartning et al. |
| 7,942,806 B2 | 5/2011 | Tracey et al. |
| 7,981,021 B2 | 7/2011 | Spitz et al. |
| 7,981,024 B2 | 7/2011 | Levy |
| 8,047,980 B2 | 11/2011 | Bartning et al. |
| 8,127,768 B2 | 3/2012 | Ziv |
| 8,177,706 B2 | 5/2012 | Bartning et al. |
| 8,221,374 B2 | 7/2012 | Hou et al. |
| 8,302,608 B2 | 11/2012 | Harmanli |
| 8,323,176 B2 | 12/2012 | Spitz et al. |
| 8,435,168 B2 | 5/2013 | Ziv et al. |
| 8,608,639 B2 | 12/2013 | Bartning et al. |
| 8,613,698 B2 | 12/2013 | Bartning et al. |
| 8,617,047 B2 | 12/2013 | Sinai et al. |
| 8,651,109 B2 | 2/2014 | Ziv et al. |
| 8,652,026 B2 | 2/2014 | Zunker et al. |
| 8,652,027 B2 | 2/2014 | Hou et al. |
| 8,753,258 B2 | 6/2014 | Bartning et al. |
| 8,911,344 B2 | 12/2014 | Altan et al. |
| 8,911,345 B2 | 12/2014 | Ziv et al. |
| 8,920,302 B2 | 12/2014 | Levy |
| 8,923,493 B2 | 12/2014 | Hillis et al. |
| 9,022,919 B2 | 5/2015 | Ellefson et al. |
| 9,050,183 B2 | 6/2015 | Bartning et al. |
| 9,078,726 B2 | 7/2015 | Karapasha |
| 9,173,768 B2 | 11/2015 | Bartning et al. |
| 9,198,748 B2 | 12/2015 | Ziv et al. |
| 9,320,640 B2 | 4/2016 | Durling |
| 9,339,361 B2 | 5/2016 | Ziv et al. |
| 9,339,363 B2 | 5/2016 | Ziv et al. |
| 9,339,364 B2 | 5/2016 | Durling et al. |
| 9,393,090 B2 | 7/2016 | Karapasha |
| 9,398,984 B2 | 7/2016 | Hou et al. |
| 9,408,685 B2 | 8/2016 | Hou et al. |
| 9,439,748 B2 | 9/2016 | Durling et al. |
| 9,549,798 B2 | 1/2017 | Sinai et al. |
| 9,597,222 B2 | 3/2017 | Durling et al. |
| 9,655,769 B2 | 5/2017 | Ziv et al. |
| 2002/0083949 A1 | 7/2002 | James |
| 2005/0113228 A1 | 5/2005 | Marcotte |
| 2007/0203429 A1 * | 8/2007 | Ziv ............. A61F 2/005 600/573 |
| 2008/0033230 A1 | 2/2008 | Bartning et al. |
| 2008/0281149 A1 | 11/2008 | Sinai et al. |
| 2009/0318750 A1 | 12/2009 | Ziv et al. |
| 2010/0218359 A1 * | 9/2010 | Bartning ............. A61F 2/005 29/428 |
| 2011/0295058 A1 * | 12/2011 | Henriksson ............. A61F 2/005 600/37 |
| 2012/0136199 A1 | 5/2012 | Hou et al. |
| 2012/0259162 A1 | 10/2012 | Karapasha |
| 2012/0259166 A1 | 10/2012 | Karapasha |
| 2012/0259167 A1 | 10/2012 | Karapasha et al. |
| 2012/0271098 A1 | 10/2012 | Ziv et al. |
| 2013/0053627 A1 * | 2/2013 | Bercovich ............. A61F 2/005 600/31 |
| 2013/0192606 A1 | 8/2013 | Ziv et al. |
| 2015/0297392 A1 | 10/2015 | Karapasha |
| 2015/0305844 A1 | 10/2015 | Schuman et al. |
| 2016/0015500 A1 | 1/2016 | Ziv et al. |
| 2016/0220342 A1 | 8/2016 | Ziv et al. |
| 2016/0235583 A1 | 8/2016 | Durling et al. |
| 2016/0296379 A1 | 10/2016 | Brown et al. |
| 2016/0296380 A1 | 10/2016 | Graham et al. |
| 2016/0374788 A1 | 12/2016 | Ramachandra et al. |
| 2017/0014217 A1 | 1/2017 | Patrusky |
| 2017/0100278 A1 | 4/2017 | Ziv et al. |

* cited by examiner

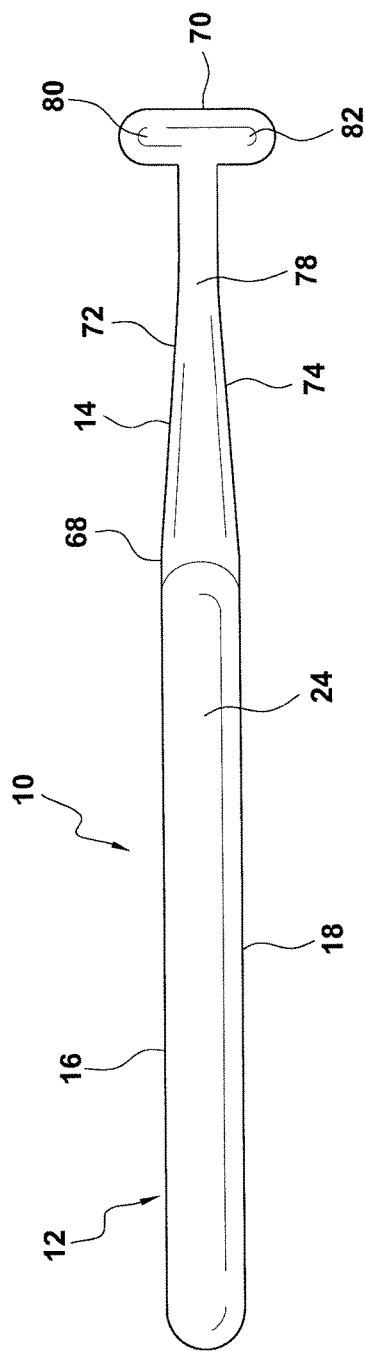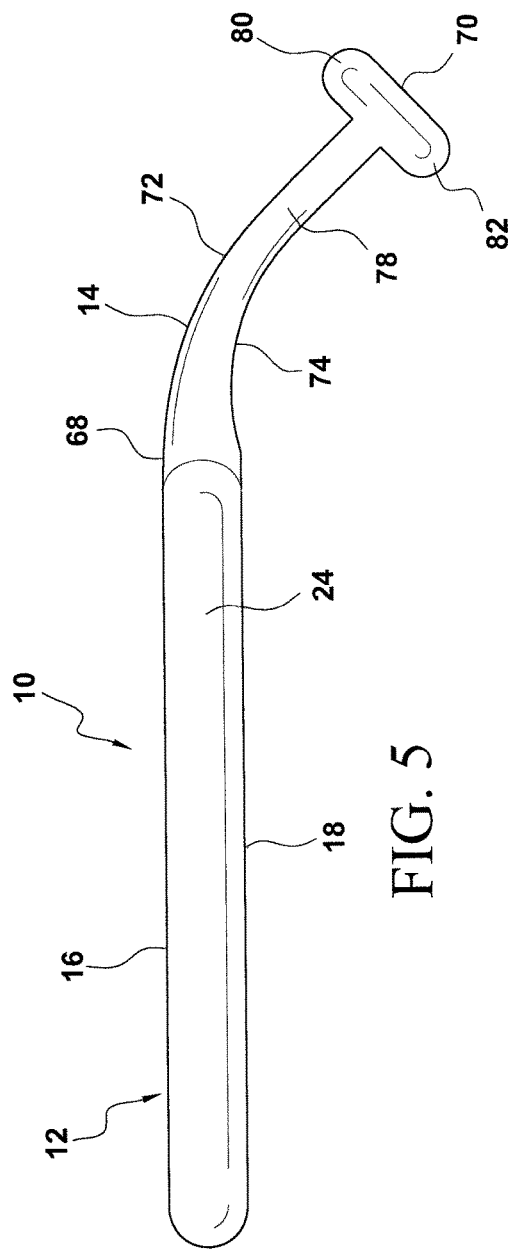
FIG. 4
FIG. 5

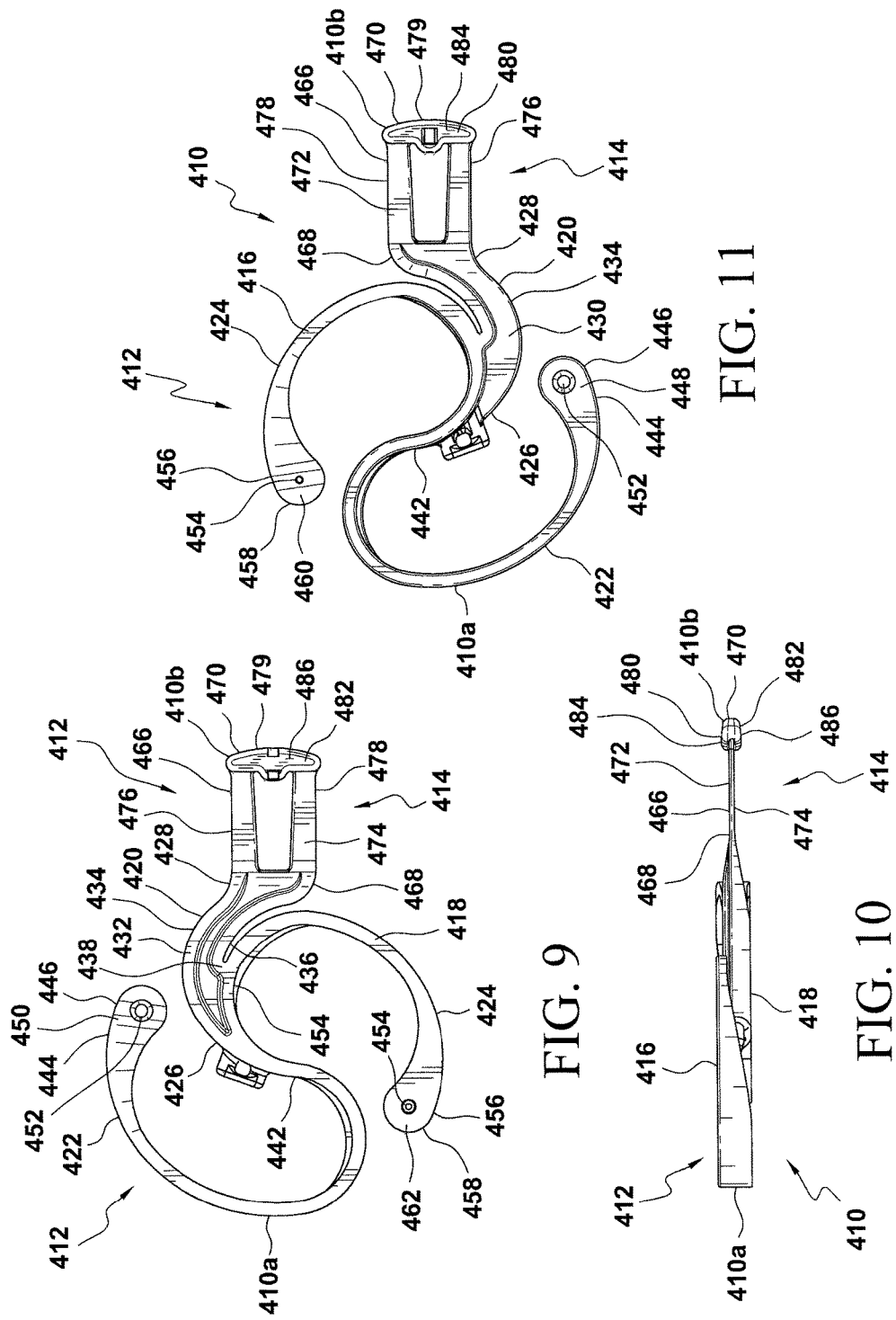

INCONTINENCE DEVICE

CROSS REFERENCE TO RELATED APPLICATION

This application claims the benefit of U.S. Patent Application Ser. No. 62/366,468, entitled "STRESS INCONTINENCE DEVICE," filed Jul. 25, 2016.

BACKGROUND OF THE INVENTION

1. Field of the Invention

The present invention generally relates to an incontinence device.

2. Description of the Related Art

By way of background, it is well appreciated that the female pelvic region includes portions of the female reproductive system, female gastrointestinal system and the female urinary system. The female pelvic region is shown in FIG. 1, and includes a vagina 200, a cervix 210, a uterus 212, a urethra 208, a bladder 214 and a symphysis pubis 216. The vagina 200 includes an introital opening 218 that exits the human body and contains a vaginal canal 202 extending from the introital opening 218 to the cervix 210. The vaginal canal 202 has a length that ranges from between about 4 to about 6 inches in most women. The cervix 210 is the entrance to the uterus and is located between the upper aspect of the vaginal canal 202 and the uterus 212. The vaginal canal 202 has an inner periphery 220.

The inner periphery 220 of the vaginal canal 202 is composed of a right lateral wall 222, a left lateral wall (not shown), an anterior wall 206, and a posterior wall 204. The four walls encompass the entire 360 degrees of the inner periphery 220. The anterior wall 206 is located closest to the urethra 208 and the urethra 208 is located between the symphysis pubis 216 and the vagina 200.

The vaginal canal 202 is commonly divided into three approximately equal sections, each representing about one-third of the overall length. Each section is approximately 2 inches in length. The inferior third 236 of the vaginal canal 202 is the most important section for alleviating female urinary incontinence because of its proximity to the urethra 208. The inferior third 236 of the vaginal canal 202 is the location affected by placement of vaginal insert devices which alleviate conditions of female incontinence, regardless of where in the vagina 202 the bulk of the device rests after insertion. In the erect female, the middle third 237 of the vaginal canal 202 is horizontally offset from the inferior third 236 of the vaginal canal 202 which is substantially parallel to the urethra 208. The urethra 208 is situated between the inferior third 236 of the vaginal canal 202 and the symphysis pubis 216, which is a bony structure situated adjacent to a front portion of the human torso and may be referred to as the bladder neck region.

The urethra 208, also referred to as a urethral tube, is a hollow tubular structure positioned anterior to the vaginal canal 202. The urethra 208 extends from a first opening 226 that exits the human body to a second opening 228 situated at the lower surface of the bladder 214. The posterior urethrovesical angle is formed where the urethra 208 enters the bladder 214. The urethra 208 has a length of about 1.5 inches in most women. The urethra 208 functions to discharge urine, which is temporarily stored in the bladder 214, from the human body. The urethra 208 has a plurality of urethral sphincter muscles 232 located along the length of its inner periphery. The urethral sphincter muscles 232 are situated below the opening 228 and are ring like muscles that normally maintain constriction of the urethra 208 to prevent the passage of urine. The relaxation of the urethral sphincter muscles 232 by normal physiological functioning will permit urine to be voluntarily expelled from the body.

The pubococcygeal muscle 233 originates at the symphysis pubis 216 and extends to the inferior extent of the coccyx 234 with a passage in the center of the muscle through which the rectum 235, vagina 200 and urethra 208 pass. The posterior portion of the passage through the pubococcygeal muscle 233 normally provides support to the posterior portion of the urethra 208 through the soft tissues of the rectum 235 and vagina 200 which assist in maintaining constriction of the urethra 208 to prevent the passage of urine. When the pubococcygeal muscle 233 stretches due to childbirth or generally relaxes due to the normal aging process, support to the posterior portion of the urethra 208 is reduced and unintentional flow of urine through the urethra 208 may occur, particularly when pressure is applied to the bladder 214 during a cough or other abdominal contraction. This condition is known as stress incontinence. Replacing or supplementing support to the posterior side of the urethra 208 can help to prevent the unintentional flow of urine through the urethra 208.

SUMMARY OF THE INVENTION

It is, therefore, an object of the present invention to provide an incontinence device insertable into and removable from a vaginal canal of a human user to apply pressure upon a urethra. The incontinence device includes a distal body member having a central core, a first arcuate arm on a first side of the central core and a second arcuate arm on a second opposite side of the central core. The first and second arcuate arms flex inward toward the central core into a first compressed position during insertion and expand outward away from the central core into a second in use position to fill the space in the middle and superior thirds of the vaginal canal in order to retain the incontinence device in the vaginal canal. The incontinence device also includes a proximal pressure member extending from the body member for resilient movement relative to the body member; wherein the pressure member applies pressure to support the urethra for controlling incontinence.

It is also an object of the present invention to provide an incontinence device including a cord attached to the first and second arcuate arms used to remove the incontinence device from the vaginal canal.

It is another object of the present invention to provide an incontinence device including an actuation mechanism composed a single flexible cord connected to both the first and second arcuate arms as well as the central core and the pressure member such that when the cord is pulled the arcuate arms move toward the central core into the first compressed position.

It is a further object of the present invention to provide an incontinence device wherein the body member is S-shaped.

It is also an object of the present invention to provide an incontinence device wherein the incontinence device is symmetrical such that upper or lower surfaces of the body member may be placed in direct contact with a posterior wall of the vaginal canal during deployment such that if inserted upside down the incontinence device will not cause any harm to the human user.

It is another object of the present invention to provide an incontinence device wherein the pressure member varies in thickness as it extends from the body member to an uncoupled second end of the pressure member.

It is a further object of the present invention to provide an incontinence device wherein the uncoupled second end of the pressure member further includes protrusions on opposite sides thereof.

It is also an object of the present invention to provide an incontinence device wherein the thickness of the pressure member tapers as the pressure member extends away from the body member.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 4 is a side elevation view of the incontinence device shown in FIG. 2 in its relaxed orientation.

FIG. 5 is a side elevation view of the incontinence device shown in FIG. 2 in its flexed orientation.

FIG. 9 is a bottom view of the embodiment shown in FIG. 8 with the cord removed.

FIG. 10 is a top view of the embodiment shown in FIG. 8 with the cord removed.

FIG. 11 is a side view of the embodiment shown in FIG. 8 with the cord removed.

DESCRIPTION OF THE PREFERRED EMBODIMENTS

Figure 1:
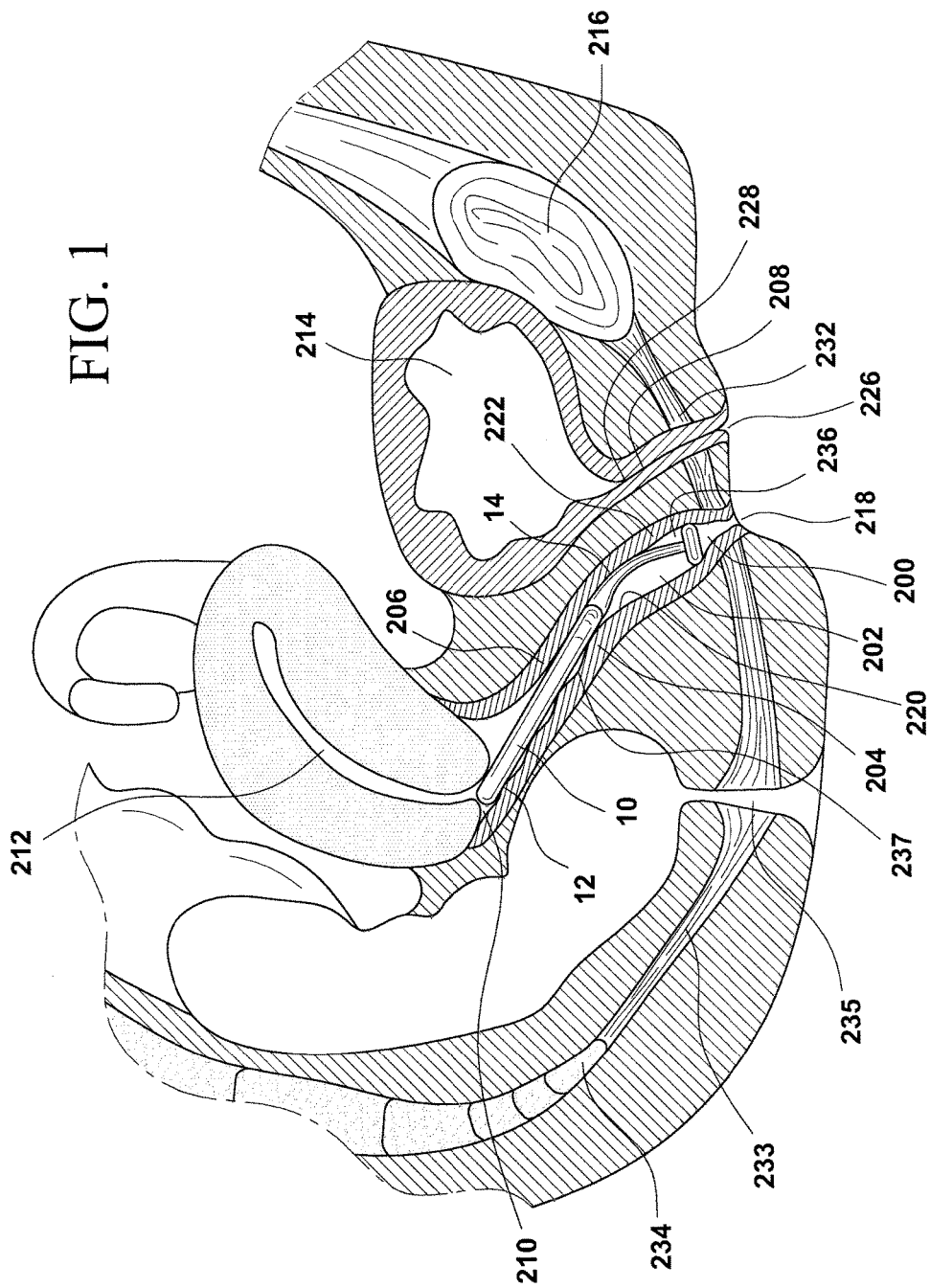
FIG. 1 a cross section view of the female pelvic region with the present incontinence device inserted.
Figure 2:
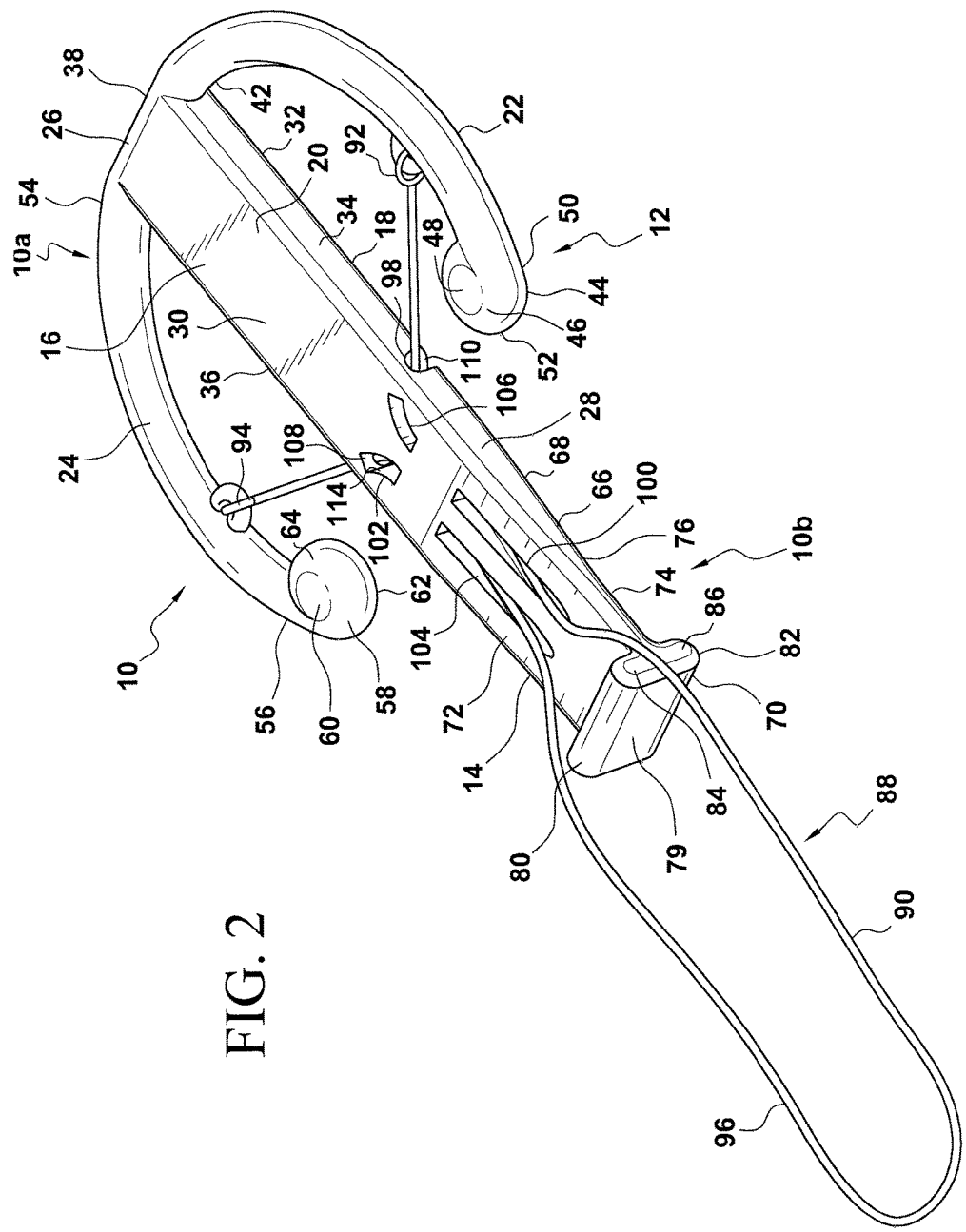
FIG. 2 is a top perspective view of the incontinence device.
Figure 3:
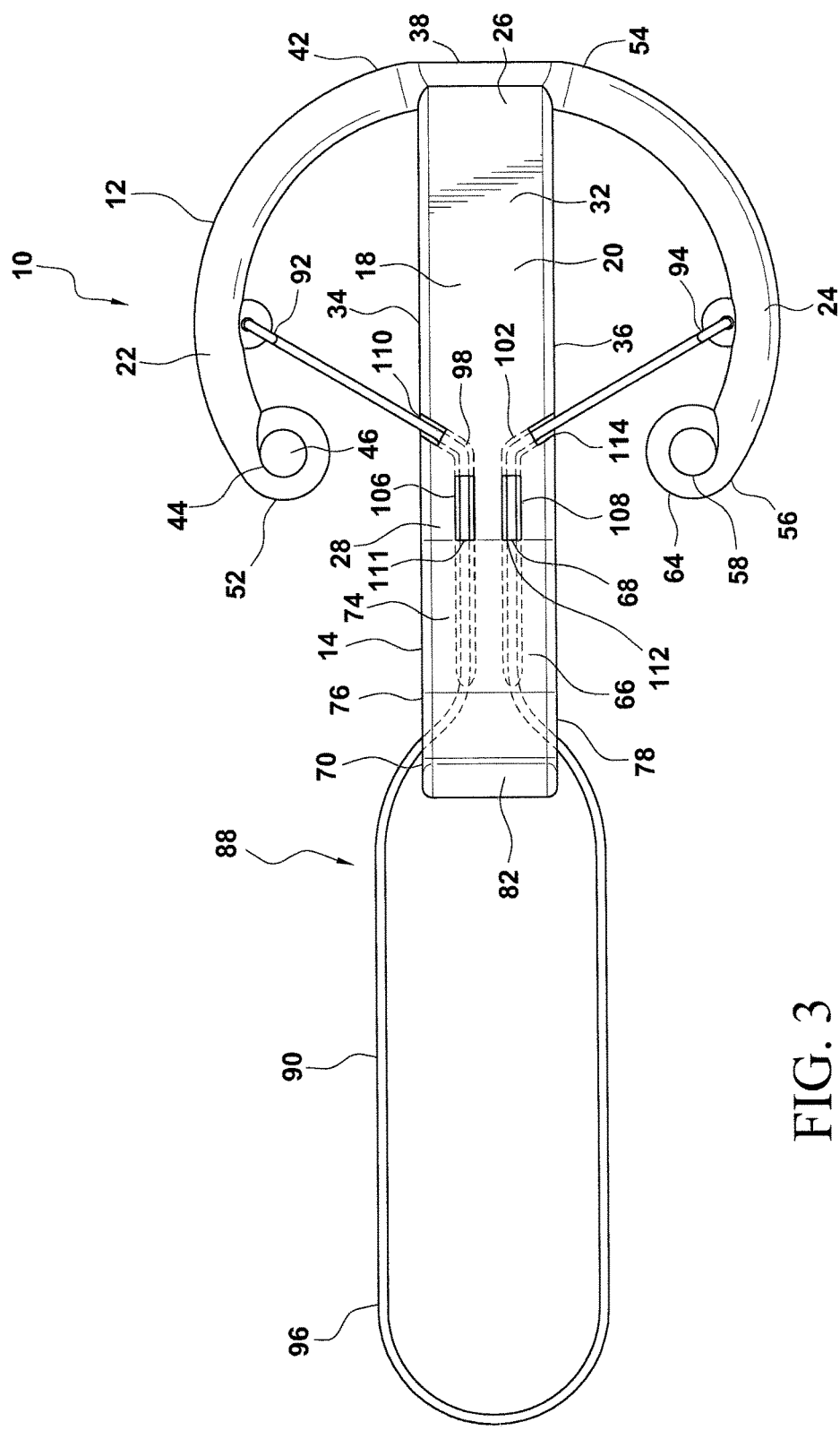
FIG. 3 is a bottom view of the incontinence device shown in FIG. 2.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 5, and with the female pelvic anatomy as described above with reference to FIG. 1 in mind, the present stress incontinence device 10 is adapted for positioning such that the second end 10b rests in plane of pubococccygeal muscle 233 with the remainder of the stress incontinence device 10 in central and superior portions of vaginal canal 202.

The stress incontinence device 10 includes distal body member 12 shaped and dimensioned for positioning upon the posterior wall 204 of the vaginal canal 202 and a proximal pressure member 14 extending from the body member 12 for movement relative to the body member 12 such that the pressure member 14 can be used to apply support to the anterior wall 206 of the inferior third 236 of the vaginal canal 202 in the approximate plane of the pubococcygeal muscle 233 and ultimately to the urethra 208 for controlling incontinence. In particular, once the stress incontinence device 10 is properly located within the vaginal canal 202, the pressure member 14, due to anatomical bend and the inherent resilience of the stress incontinence device 10, places pressure on the anterior wall 206 of the vaginal canal 202 and ultimately the urethra 208 for controlling incontinence. Because of resilience of the pressure member 14 and the anatomical shape of the vaginal canal 202 in the erect female, the pressure member 14 exhibits a spring like affect, due to the variable thickness of the pressure member 14 as it extends toward the second end 10b of the stress incontinence device, that results in the application of pressure on the urethra 208. In accordance with a preferred embodiment, the stress incontinence device 10 is composed of flexible, biocompatible polymeric or elastomeric materials such as polyolefins, acetel, silicone, urethane, ABS, or various thermoplastic elastomers and/or combination of materials producing the desired spring-like pressure to support the urethra.

The body member 12 is positioned at the first end 10a of the stress incontinence device 10 and the pressure member 14 is positioned at the second end 10b of the stress incontinence device 10. The body member 12 is substantially flat along its upper and lower surfaces 16, 18 such that the upper surface 16 lies in a first plane and the lower surface 18 lies in a second plane that is substantially parallel to the first plane. It should be appreciated that although the body member 12 is described as being substantially flat, the surfaces of the body member may be contoured to allow consistent wall thickness for injection molding although the upper and lower surfaces will, however, generally lie in two parallel planes. Most importantly, the central core 20 is structured to remain generally straight in use while the pressure member 14 flexes in accordance with the present invention. As will be appreciated based upon the following disclosure, the body member 12 is constructed with a substantially symmetrical configuration such that the upper or lower surfaces 16, 18 of the body member 12 may be placed in direct contact with the posterior wall 204 of the vaginal canal 202 during deployment with no negative effects.

The body member 12 is substantially composed of three elements, a central core 20, a first arcuate arm 22, and second arcuate arm 24. The central core 20 is an elongated member including a first end 26 and a second end 28. The central core 20 also includes an upper surface 30, a lower surface 32, first and second lateral side walls 34, 36 extending between the upper and lower surfaces 30, 32, and a first end wall 38.

The first arcuate arm 22 includes a first end 42 secured to the first end 26 of the central core 20 and a second end 44 positioned adjacent the second end 28 of the central core 20. The first arcuate arm 22 extends about an arc of approximately 90 degrees to 140 degrees, and preferably 125 degrees. The first arcuate arm 22 includes a circular cross sectional profile as it extends from the first end 42 thereof toward the second end 44 of the first arcuate arm 22. While a circular cross sectional profile is disclosed herein, it is appreciated the first arcuate arm could have an ovoid or rectangular cross section.

The first arcuate arm 22 is provided with a rounded protuberance 46 at the second end 44 thereof. The rounded protuberance 46 includes upper and lower surfaces 48, 50 that respectively align with the upper and lower surfaces 30, 32 of the central core 20. The rounded protuberance 46 also includes a curved outer wall 52 extending between the upper and lower surfaces 48, 50 thereof.

The second arcuate arm 24 includes a first end 54 secured to the first end 26 of the central core 20 and a second end 56 positioned adjacent the second end 28 of the central core 20. The second arcuate arm 24 extends about an arc of approximately 90 degrees to 140 degrees, and preferably 125 degrees. The second arcuate arm 24 includes a circular cross sectional profile as it extends from the first end 54 thereof toward the second end 56 of the second arcuate arm 24. As with the first arcuate arm 22, the second arcuate arm 24 may have an ovoid or rectangular cross section.

The second arcuate arm 24 is provided with a rounded protuberance 58 at the second end 56 thereof. The rounded protuberance 58 includes upper and lower surfaces 60, 62 that respectively align with the upper and lower surfaces 30, 32 of the central core 20. The rounded protuberance 58 also includes a curved outer wall 64 extending between the upper and lower surfaces 60, 62 thereof. While rounded protuberances are disclosed at the ends of the first and second arcuate arms, the protuberances may exhibit various shapes so long as they have smooth radiused edges so as to not cause discomfort.

Figure 6:
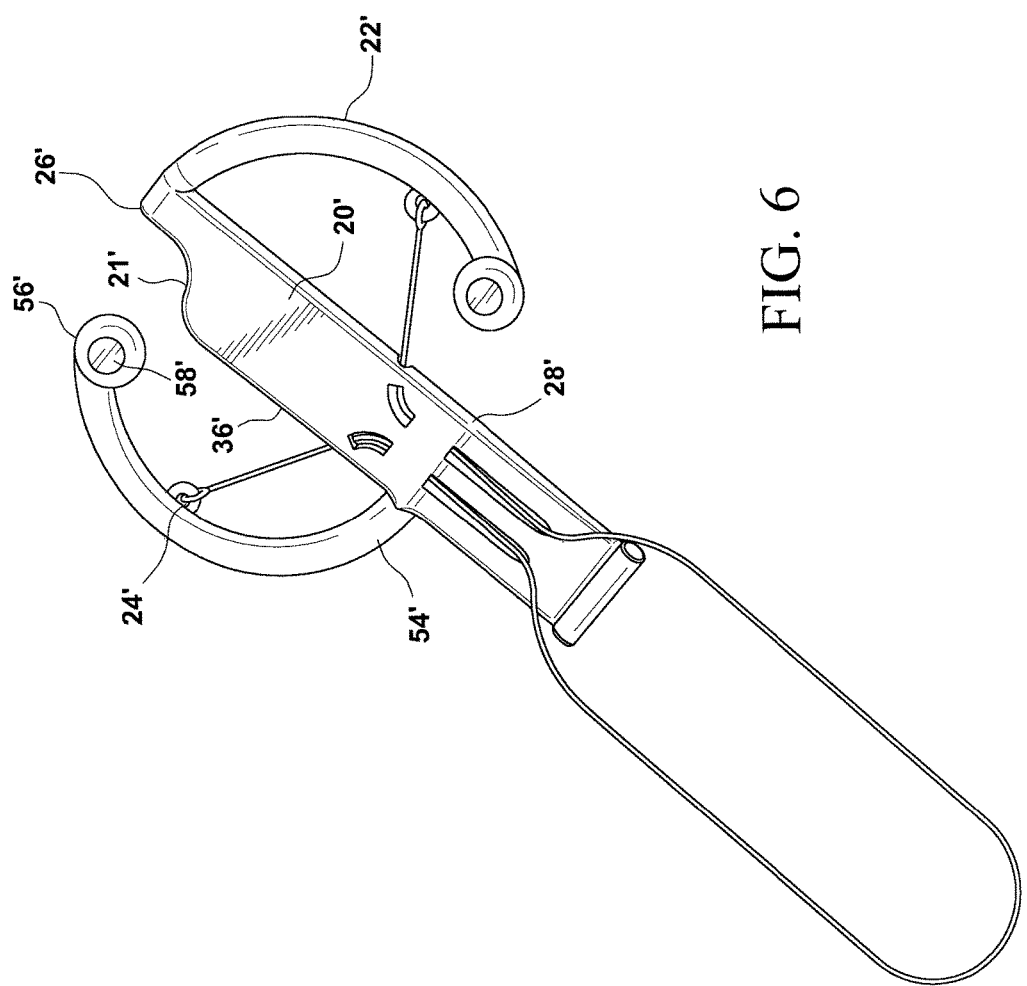
FIG. 6 is a perspective view of the incontinence device in accordance with an alternate embodiment.
Figure 7:
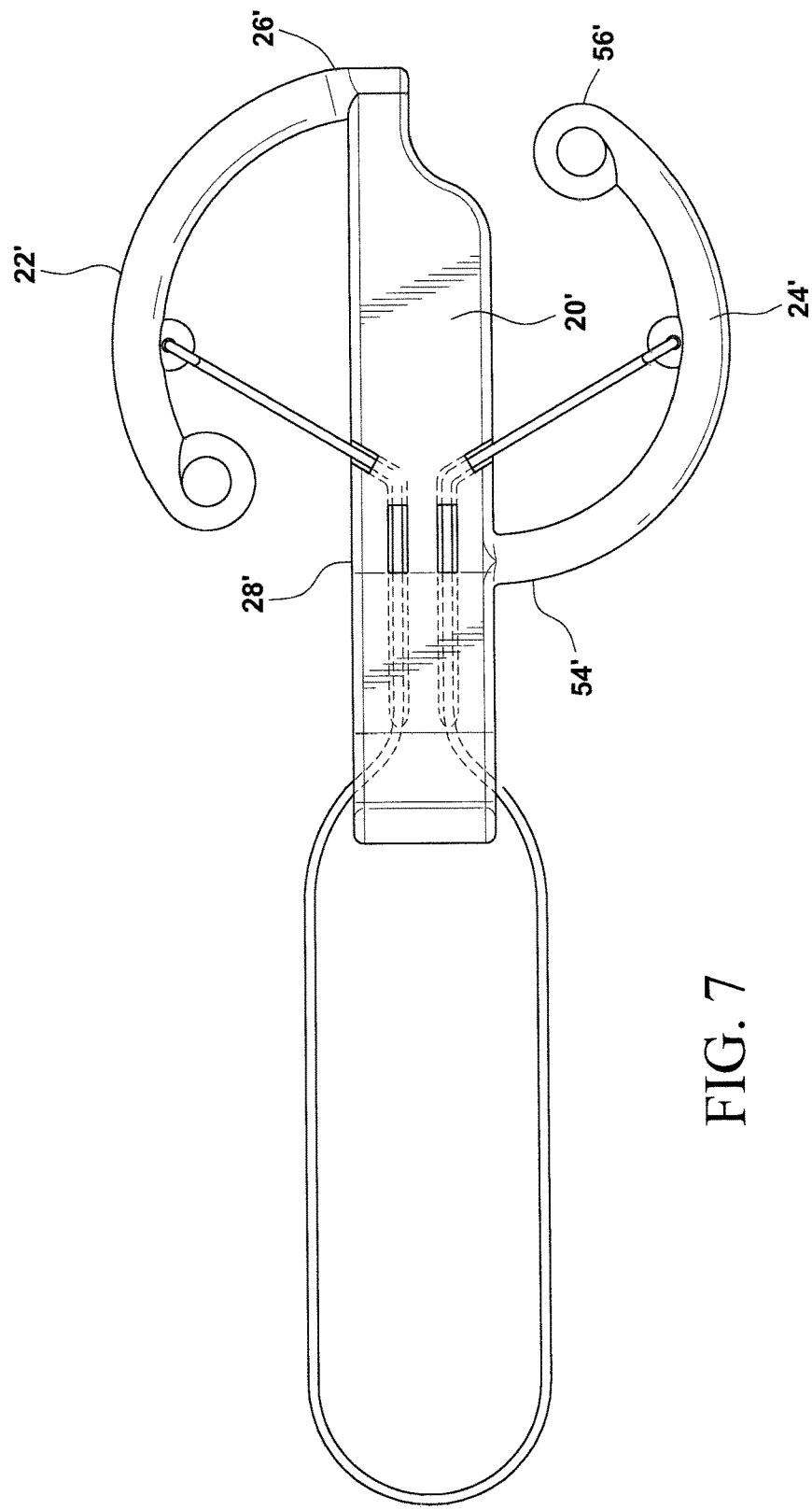
FIG. 7 is a bottom view of the incontinence device shown in FIG. 6.

In accordance with an alternate embodiment as shown in FIGS. 6 and 7, the orientation of the second arcuate arm 24' may be varied (while the first arcuate arm 22' remains as described above) such that it is connected at the second end 28' of the central core 20' and extends to the first end 26' of the central core 20'. In particular, the second arcuate arm 24' includes a first end 54' secured to the second end 28' of the central core 20' and a second end 56' positioned adjacent the first end 26' of the central core 20'. The arcuate shapes of the first and second arcuate arms 22', 24' form a substantially S-shaped body member.

In addition to reorienting the second arcuate arm 24', this embodiment also includes a recess 21' at the first end of the central core 20' along the second lateral side wall 36'. The recess 21' is shaped and dimensioned to receive the rounded protuberance 58' at the second end 56' of the second arcuate arm 24' when the second arcuate arm 24' is compressed toward the central core 20 for insertion of the stress incontinence device 10 as described below.

The arcuate shapes of the first and second arcuate arms 22, 24 allow for flex of the first and second arcuate arms 22, 24 relative to the central core 20 during insertion (or retrieval) of the stress incontinence device 10 into (or out of) the vagina (that is, the insertion and retrieval state of the stress incontinence device 10), then expand to fill the space in the middle and superior thirds 237, 238 of the vaginal canal 202 in order to retain the device 10 in the vagina 200 (that is, the deployed state of the stress incontinence device 10). The first and second arcuate arms 22, 24 likewise flex to allow removal from the vagina 200 in a collapsed condition.

As mentioned above, the stress incontinence device 10 includes a pressure member 14 extending from the body member 12 in a manner allowing the controlled flexion of the pressure member 14 relative to the body member 12 for the purpose of applying support to the anterior wall 206 of the vaginal canal 202 and ultimately to the urethra 208 for controlling incontinence, substituting for the loss of support due to stretching of the passage through the pubococcygeal muscle 233. Although flexion of the pressure member 14 relative to body member 12 is achieved in accordance with the present invention, the stress incontinence device 10 is substantially flat when in its relaxed configuration and will exhibit a bent configuration when used as shown in FIG. 1.

The ability to flex provides for the inherent bias (that is, stored energy resulting from resilience of the pressure member 14) necessary to provide support along the anterior wall 206 of the vaginal canal 202.

The pressure member 14 is an elongated member 66 including a first end 68 coupled to the second end 28 of the central core 20 and an uncoupled second end 70. The elongated member 66 also includes an upper surface 72, a lower surface 74, first and second lateral side walls 76, 78 extending between the upper and lower surfaces 72, 74, and an end wall 79 at the second end 70.

The first end 68 of the pressure member 14 is secured to the second end 70 of the central core 20. The junction of the central core 20 and pressure member 14 flexion point from which the pressure member 14 flexes along its length in use allowing for relative movement between the body member 12 and pressure member 14 in a manner creating the inherent bias of the stress incontinence device 10 required in accordance with the present invention. Since the body member 12 sits upon the posterior wall 204 of the vaginal canal 202, relative movement results from the pressure member 14 flexing beginning at the junction of the central core 20 and the pressure member 14 such that the second end 70 of the pressure member 14 moves into contact with the anterior wall 206 of the vaginal canal 202.

The shape of the pressure member 14 allows for the application of pressure in a controlled manner. In particular, the second end 68 of the pressure member 14 is provided with elongated protrusions 80, 82 along the upper and lower surfaces 72, 74 thereof. The upper protrusion 80 extends a desired distance above the upper surface 72 of the pressure member 14 while the lower protrusion 82 extends a desired distance above the lower surface 74 of the pressure member 14.

The upper protrusion 80 and the lower protrusion 82 are similarly shaped. They each extend from the first lateral wall 76 to the second lateral wall 78 of the pressure member 14 at a position adjacent to the second end 70 of the pressure member 14. While the lateral walls 84, 86 of the upper and lower protrusions 80, 82 are substantially flat, the surface extending between the lateral walls 84, 86 has a semi-circular profile when viewed along a cross section taken along the longitudinal axis of the pressure member 14 (that is, the axis extending between the first end 68 and the second end 70 of the pressure member 14). It is appreciated that while preferred protrusions are shown in the various figures, the degree to which the protrusions extend outwardly may be varied depending upon specific anatomical needs.

It is also appreciated that the pressure member 14 is preferably tapered in thickness as it extends from the first end 68 to the second end 70 so as to have the strength to place pressure on the urethra 208. The taper can be either symmetrical or non-symmetrical for applying a desired pressure.

The stress incontinence device 10 is designed such that if inserted upside down the stress incontinence device 10 will not cause any harm to the user. It particular, because the stress incontinence device 10 is symmetrical (when unstressed as show in FIG. 4) about the general plane of the device, that is, the plane between the upper and lower surfaces of the stress incontinence device 10, it reacts and functions identically, regardless of which side is up; that is, there is not a top or bottom. With this in mind, it is appreciated relative terms such as upper, lower, etc. are used throughout the present disclosure, and these terms are merely used in reference to the various drawings employed in disclosing the present invention.

The stress incontinence device 10 is further provided with an actuation mechanism 88 for controlling the flexion of the first and second arcuate arms 22, 24 relative to the central core 20 so as to allow for one to pull the first and second arcuate arms 22, 24 toward the central core 20 to reduce the profile of the stress incontinence device 10 and make transition through the opening of the vagina easier. The actuation mechanism 88 is composed a single flexible cord 90 connected to both the first and second arcuate arms 22, 24, as well as the central core 20 and the pressure member 14. The cord 90 includes a first end 92 secured to a central position along the length of the first arcuate arm 22 and a second end 94 secured to a central position along the length of the second arcuate arm 24. The remainder of the cord 90 is threaded through various channels formed in the central core 20 and the pressure member 14 so as to create a looped portion 96 (that is, a central segment of the cord 90 between the first end 92 and the second end 94) that may be manipulated by a user to cause controlled movement of the first and second arcuate arms 22, 24.

The central core 20 is provided with a first lateral channel 98 extending between the first lateral side wall 34 of the central core 20 and the second end 28 of the central core 20 where the first lateral channel 98 transitions into a first guiding groove 100 formed in the upper surface 72 of the pressure member 14. The central core 20 is also provided with a second lateral channel 102 extending between the second lateral side wall 36 of the central core 20 and the second end 28 of the central core 20 where the second lateral channel 102 transitions into a second guiding groove 104 formed in the upper surface 72 of the pressure member 14. The first and second lateral channels 98, 102 are provided with access openings 106, 108 allowing one to view the cord 90 as its passes therethrough.

Considering the cord 90 as it extends form the first end 92 thereof to the second end 94 thereof, the first end 92 is secured to a central section along the interior surface of the first arcuate arm 22. The cord 90 then extends through an aperture 110 formed in the first lateral wall 34 and into the first lateral channel 98. The cord 90 exits the first lateral channel 98 at an aperture 111 in the second end 28 of the central core 20, and extends into the first guiding groove 100. Upon exiting the first guiding groove 100, the cord 90 forms the loop portion 96 and then extends into the second guiding groove 104. After passing through the second guiding groove 104, the cord 90 extends through an aperture 112 formed in the second end 28 of central core 20 and into the second lateral channel 102. The cord 90 then extends through the second lateral channel 102 until it exits the second lateral channel 102 at an aperture 114 formed in the second lateral side wall 36 of the central core 20. From the second lateral side wall 36 the cord 90 extends to its second end 94 that is secured to the interior surface of the second arcuate arm 24.

Figure 8:
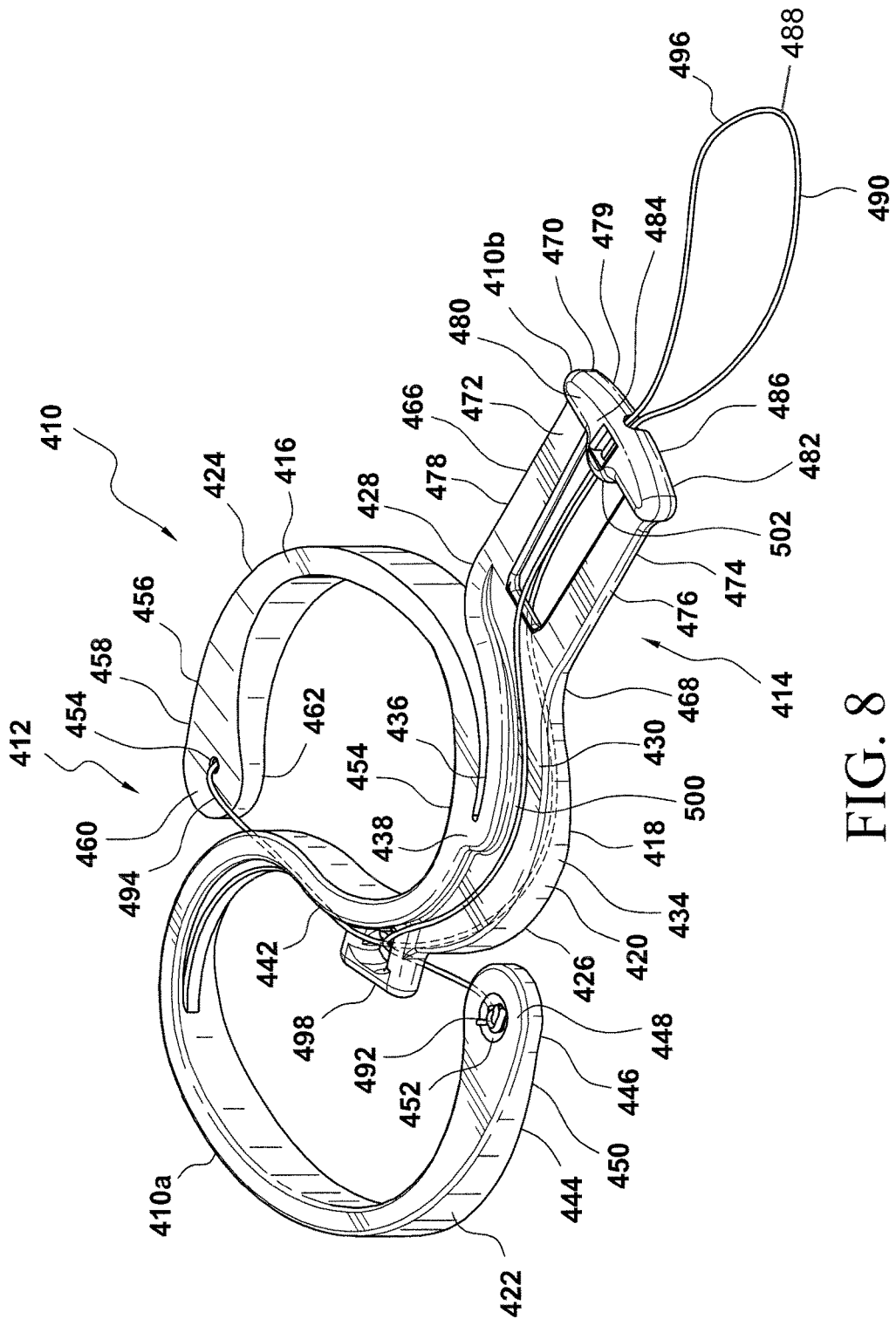
FIG. 8 is a top perspective of an alternate embodiment an incontinence device.

In accordance with another embodiment of the present invention as shown in FIGS. 8 and 9, and as with the embodiments previously described, this alternate embodiment provides a incontinence device 410 adapted for positioning such that the second end 410b rests in plane of pubococccygeal muscle 233 with the remainder of the incontinence device 410 in central and superior portions of vaginal canal 202.

The incontinence device 410 includes a distal body member 412 shaped and dimensioned for positioning upon the posterior wall 204 of the vaginal canal 202 and a proximal pressure member 414 extending from the body member 412 for movement relative to the body member 412 such that the pressure member 414 can be used to apply support to the anterior wall 206 of the inferior third 236 of the vaginal canal 202 in the approximate plane of the pubococcygeal muscle 233 and ultimately to the urethra 208 for controlling incontinence. In particular, once the incontinence device 410 is properly located within the vaginal canal 202, the pressure member 414, due to anatomical bend and the inherent resilience of the incontinence device 410, places pressure on the anterior wall 206 of the vaginal canal 202 and ultimately the urethra 208 for controlling incontinence. Because of resilience of the pressure member 414 and the anatomical shape of the vaginal canal 202 in the erect female, the pressure member 414 exhibits a spring like affect, due to the variable thickness of the pressure member 414 as it extends toward the second end 410b of the stress incontinence device, that results in the application of pressure on the urethra 208. In accordance with a preferred embodiment, the incontinence device 410 is composed of flexible, biocompatible polymeric or elastomeric materials such as polyolefins, acetel, silicone, urethane, ABS, or various thermoplastic elastomers and/or combination of materials producing the desired spring-like pressure to support the urethra.

The body member 412 is positioned at the first end 410a of the incontinence device 410 and the pressure member 414 is positioned at the second end 410b of the incontinence device 410b. The body member 412 is substantially flat such that its upper surface 416 predominantly lies in a first plane and its lower surface 418 predominantly lies in a second plane that is substantially parallel to the first plane. It should be appreciated that although the body member 412 is described as being substantially flat, the surfaces of the body member may be contoured to allow for desired flexion for the purpose of insertion and retrieval from the vaginal canal of a human user. Most importantly, the central core 420 is structured to remain generally straight in use while the pressure member 414 flexes in accordance with the present invention. As will be appreciated based upon the following disclosure, the body member 412 is constructed such that the upper or lower surfaces 416, 418 of the body member 412 may be placed in direct contact with the posterior wall 204 of the vaginal canal 202 during deployment with no negative effects.

The body member 412 is substantially composed of three elements, a central core 420, a first arcuate arm 422, and second arcuate arm 424. The central core 420 is an elongated member including a first end 426 and a second end 428. The central core 420 also includes an upper surface 430, a lower surface 432, first and second lateral side walls 434, 436 extending between the upper and lower surfaces 430, 432, and a first end wall 438. As will be appreciated based upon the following disclosure, the central core 420 includes a curved construction as it extends from its first end 426 to its second end 428. This curved construction allows for ideal position of the first and second arcuate arms 422, 424 as they extend from the first end 426 of the central core 420.

The first arcuate arm 422 includes a first end 442 secured to the first end 426 of the central core 420 and a second end 444 positioned adjacent the first end 426 of the central core 420, but on a side of the central core 420 opposite the position in which the first end 442 of the first arcuate arm 422 extends. The first arcuate arm 422 extends from the first end 426 of the central core 420 in a counter-clockwise direction away from both the first end 426 and the second end 428 of the central core 420 to form a loop positioned beyond the first end 426 of the central core 420 where the first arcuate arm 422 ends with its second end 444 located adjacent to the first end 426 of the central core 420. It may therefore be thought of that the first arcuate arm 422 thereby lies on a first side of the central core 420. In accordance with a preferred embodiment the first arcuate arm 422 extends about a loop of approximately 350°.

The first arcuate arm 422 includes a rectangular cross sectional profile as it extends from the first end 442 thereof toward the second end 444 of the first arcuate arm 422. While a rectangular cross sectional profile is disclosed herein, it is appreciated the first arcuate arm could have an ovoid or circular cross section.

The first arcuate arm 422 is provided with a rounded protuberance 446 at the second end 444 thereof. The rounded protuberance 446 includes upper and lower surfaces 448, 450. An aperture 452 is formed in the rounded protuberance 446 and extends from the upper surface 448 to the lower surface 450.

The second arcuate arm 424 includes a first end 454 secured to the first end 426 of the central core 420 and a second end 456 positioned adjacent the first end 426 of the central core 420 and the first end 442 of the first arcuate arm 422 on the same side of the central core 420 from which the first end 454 of the second arcuate arm 424 extends. That is, when viewed as shown in FIG. 11, the second arcuate arm 424 extends from the first end 426 of the central core 420 in a counter-clockwise direction away from the first end 426 and toward the second end 428 of the central core 420 to form a loop positioned, for a portion of its segment, along the curvature of the central core 420 where the second arcuate arm 424 ends with its second end 456 located adjacent to the first end 426 of the central core 420. It may therefore be thought of that the second arcuate arm 424 thereby lies on a second side of the central core 420, opposite the first side on which the first arcuate arm lies 422. In accordance with a preferred embodiment the second arcuate arm 424 extends about a loop of approximately 350°. Based upon the arcuate orientations of the first and second arcuate arms 422, 424 and their connection to one another via the central core 420, a substantial S-shaped body is formed.

The second arcuate arm 424 includes a rectangular cross sectional profile as it extends from the first end 454 thereof toward the second end 456 of the second arcuate arm 424. While a rectangular cross sectional profile is disclosed herein, it is appreciated the first arcuate arm could have an ovoid or circular cross section.

The second arcuate arm 424 is provided with a rounded protuberance 458 at the second end 456 thereof. The rounded protuberance 458 includes upper and lower surfaces 460, 462. An aperture 454 is formed in the rounded protuberance 458 and extends from the upper surface 460 to the lower surface 462.

As with the prior embodiments, the arcuate shapes of the first and second arcuate arms 422, 424 allow for flex of the first and second arcuate arms 422, 424 relative to the central core 420 during insertion (or retrieval) of the incontinence device 410 into (or out of) the vagina (that is, the insertion and retrieval state of the incontinence device 410), then expand to fill the space in the middle and superior thirds 237, 238 of the vaginal canal 202 in order to retain the incontinence device 410 in the vagina 200 (that is, the deployed state of the incontinence device 410). The first and second arcuate arms 422, 424 likewise flex to allow removal from the vagina 200 in a collapsed condition.

The incontinence device 410 includes a pressure member 414 extending from the body member 412 in a manner allowing the controlled flexing of the pressure member 414 relative to the body member 412 for the purpose of applying support to the anterior wall 206 of the vaginal canal 202 and ultimately to the urethra 208 for controlling incontinence, substituting for the loss of support due to stretching of the passage through the pubococcygeal muscle 233. Although flexing of the pressure member 414 relative to body member 412 is achieved in accordance with the present invention, the incontinence device 410 is substantially flat when in its relaxed configuration and will exhibit a bent configuration when in use similar to that shown with reference to the embodiment shown in FIG. 5. The ability to flex provides for the inherent bias (that is, stored energy resulting from resilience of the pressure member 414) necessary to provide support along the anterior wall 206 of the vaginal canal 202.

The pressure member 414 is an elongated member 466 including a first end 468 coupled to the second end 428 of the central core 420 and an uncoupled second end 470. The elongated member 466 also includes an upper surface 472, a lower surface 474, first and second lateral side walls 476, 478 extending between the upper and lower surfaces 472, 474, and an end wall 479 at the second end 470.

The first end 468 of the pressure member 414 is secured to the second end 428 of the central core 420. The junction of the central core 420 and pressure member 414 defines a flexion point from which the pressure member 414 flexes along its length in use allowing for relative movement between the body member 412 and pressure member 414 in a manner creating the inherent bias of the incontinence device 410 required in accordance with the present invention. Since the body member 412 sits upon the posterior wall 204 of the vaginal canal 202, relative movement results from the pressure member 414 flexing beginning at the junction of the central core 420 and the pressure member 414 such that the second end 470 of the pressure member 414 moves into contact with the anterior wall 206 of the vaginal canal 202.

The shape of the pressure member 414 a lows for the application of pressure in a controlled manner. In particular, the second end 468 of the pressure member 414 is provided with elongated protrusions 480, 482 along the upper and lower surfaces 472, 474 thereof. The upper protrusion 480 extends a desired distance above the upper surface 472 of the pressure member 414 while the lower protrusion 482 extends a desired distance above the lower surface 474 of the pressure member 414.

The upper protrusion 480 and the lower protrusion 482 are similarly shaped. They each extend from the first lateral wall 476 to the second lateral wall 478 of the pressure member 414 at a position adjacent to the second end 470 of the pressure member 414. While the lateral walls 484, 486 of the upper and lower protrusions 480, 482 are substantially flat, the surface extending between the lateral walls 484, 486 has a semi-circular profile when viewed along a cross section taken along the longitudinal axis of the pressure member 414 (that is, the axis extending between the first end 468 and the second end 470 of the pressure member 414). It is appreciated that while preferred protrusions are shown in the various figures, the degree to which the protrusions extend outwardly may be varied depending upon specific anatomical needs.

It is also appreciated that the pressure member 414 is preferably tapered in thickness as it extends from the first end 468 to the second end 470 so as to have the strength to place pressure on the urethra 208. The taper can be either symmetrical or non-symmetrical for applying a desired pressure.

As with the prior embodiments, the incontinence device 410 is designed such that if inserted upside down the incontinence device 410 will not cause any harm to the user.

It reacts and functions identically, regardless of which side is up; that is, there is not a top or bottom.

The incontinence device 410 is further provided with an actuation mechanism 488 for controlling the flexion of the first and second arcuate arms 422, 424 relative to the central core 420 so as to allow for one to pull the first and second arcuate arms 422, 424 toward the central core 420 to reduce the profile of the stress incontinence device 410 and make transition through the opening of the vagina easier. The actuation mechanism 488 is composed a single flexible cord 490 connected to both the first and second arcuate arms 422, 424, as well as the central core 420 and the pressure member 414. The cord 490 includes a first end 492 secured to the aperture 452 in the first arcuate arm 422 and a second end 494 secured to the aperture 464 in the second arcuate arm 424. The remainder of the cord 490 is threaded through various channels formed in the central core 420 and the pressure member 414 so as to create a looped portion 496 (that is, a central segment of the cord 490 between the first end 492 and the second end 494) that may be manipulated by a user to cause controlled movement of the first and second arcuate arms 422, 424.

The central core 420 is provided with a first channel (or cord guide) 498 at the first end 426 of the central core 420 and a guiding groove 500 formed along the curvature of the central core 420. A second channel (or cord guide) 502 is formed at the second end 468 of the pressure member 414.

Considering the cord 490 as it extends form the first end 492 thereof to the second end 494 thereof, the first end 492 is secured to the aperture 452 in the first arcuate arm 422. The cord 490 then extends through the first channel (or cord guide) 498 at the first end 426 of the central core 420, along the guiding groove 500 formed along the curvature of the central core 420 and extends into the second channel (or cord guide) 502. Upon exiting the second channel (or cord guide) 502 the cord 490 forms the loop portion 496 and then extends into the second channel (or cord guide) 502, along the guiding groove 500 formed along the curvature of the central core 420, through the first channel (or cord guide) 498, and is ultimately secured to the aperture 464 in the second arcuate arm 424.

In practice, the stress incontinence device 10, 410 will be prepackaged in an inserter (not shown). Although not shown it is contemplated an inserter would simply be a "tubular structure" in which the stress incontinence device 10, 410 is drawn into a pre-collapsed orientation to ease initial placement into the vagina. It would then, however, need to be "pushed out" of the tube by a plunger to remain in the vagina. It is also contemplated the stress incontinence device 10, 410 may be deployed within the vaginal canal 202 by first pulling upon the loop portion 96, 496 such that it moves away from the pressure member 14, 414 causing the first and second arcuate arms 22, 24, 422, 424 to be pulled inwardly toward the central core 20, 420. While use of the actuation mechanism 88, 488 is contemplated, it is also appreciated the first and second arcuate arms 22, 24, 422, 424 may also just flex inward during insertion and flex back out once properly positioned. It is also appreciated that an intentional inward flex from the actuation mechanism 88, 488 will be more important in conjunction with the embodiments shown in FIGS. 6 to 9, as the first arcuate arm 22', 422 might "snag" during insertion.

The stress incontinence device 10, 410 may then be inserted within the vaginal canal 402 and positioned with the lower surface 18, 418 in contact with the posterior wall 204 of the vaginal canal 202. The stress incontinence device 10, 410 is inserted into the vagina 200 with the support member 12, 412 (that is, the first end 10a, 410a of the stress incontinence device 10, 410a) entering the vagina 200 first. The pressure member 14, 414 on the proximal end (that is, the second end 10b, 410b) of the stress incontinence device 10, 410 enters the vagina 200 last. The first and second arcuate arms 22, 24, 422, 424 which compress during entry into the vagina 200 expand in the deep portion of the vagina 200 which, in the erect female, is above but generally parallel to the muscles in the pelvic floor. This maintains the stress incontinence device 10, 410 in the vagina 200. The pressure member 14, 414 then sits in the deep portion of the vagina.

Once the stress incontinence device 10 is properly positioned within the vaginal canal 202, the loop portion 96, 496 is released allowing the first and second arcuate arms 22, 24, 422, 424 to move outwardly away from the central core 20, 420. The pressure member 14, 414 is then actuated to move into contact with the anterior wall 206 of the vaginal canal 202 in a manner applying pressure thereto that ultimately applies pressure to the urethra 208 for controlling incontinence; wherein the stress incontinence device 10, 410 is position within the vaginal canal 202 such that the pressure member 14, 414 can be used to apply pressure support to the anterior wall 206 of the inferior third 236 of the vaginal canal 202 in the approximate plane of the pubococcygeal muscle 233 and ultimately to the urethra 208 for controlling incontinence.

In particular, the vagina 200 of the erect female bends inferiorly and passes through the muscles of the pelvic floor. The bend of the vagina 200 in the erect female, which extends in a generally inferior and anterior direction from the deep vagina, also flexes the pressure member 14, 414 at the proximal end of the stress incontinence device 10, 410 such that the pressure member 14, 414 falls in the plane of the pelvic floor muscles. Because of the resulting bend in the stress incontinence device 10, 410, the natural tendency of the stress incontinence device 10, 410 to return to its straight condition causes the pressure member 14, 414 to place a supporting force on the posterior side of the urethra 208 in a direction that is substantially perpendicular to the lumen of the urethra 208. This support emulates the natural support of the pelvic floor muscles which prevents unintended relief of the bladder through the urethra 208 in normal, healthy physiological conditions. Because the stress incontinence device 10, 410 is generally symmetrical about a plane between the two generally "flat" sides of the stress incontinence device 10, 410, the described conditions exist regardless of which of the two generally "flat" sides of the device is facing the anterior direction during insertion into the vagina 200. Cooperation between a stress incontinence device 10, 410 positioned in the vagina 200 and the symphysis pubis 216 allows the urethra 208 to be compressed upon itself thereby providing a means to alleviate involuntary urine flow from the bladder.

While the preferred embodiments have been shown and described, it will be understood that there is no intent to limit the invention by such disclosure, but rather, it is intended to cover all modifications and alternate constructions falling within the spirit and scope of the invention.

We claim:

1. An incontinence device insertable into and removable from a vaginal canal of a human user to apply pressure upon a urethra comprising:
   a distal body member including a central core having a first end and a second end, a first arcuate arm on a first side of the central core and a second arcuate arm on a second opposite side of the central core, the first and second arcuate arms flex inward toward the central core into a first compressed position during insertion and expand outward away from the central core into a second in use position to fill middle and superior thirds of the vaginal canal in order to retain the incontinence device in the vaginal canal; and a proximal pressure member extending from the distal body member for resilient movement relative to the distal body member, the proximal pressure member includes a first end coupled to the second end of the central core and an uncoupled second end, a junction of the central core and the proximal pressure member defines a flexion point from which the proximal pressure member flexes allowing for relative movement between the distal body member and the proximal pressure member, the proximal pressure member also includes an upper surface, a lower surface, and first and second lateral side walls extending between the upper and lower surfaces, wherein a first elongated protrusion is provided along the upper surface at the second end of the proximal pressure member and a second elongated protrusion is provided along the lower surface at the second end of the proximal pressure member;

wherein the pressure member applies pressure to support the urethra for controlling incontinence.

2. The incontinence device of claim 1, further including a cord attached to the first and second arcuate arms used to remove the incontinence device from the vaginal canal.

3. The incontinence device of claim 1, including an actuation mechanism composed of a single flexible cord connected to both the first and second arcuate arms as well as the central core and the pressure member such that when the cord is pulled the arcuate arms move toward the central core into the first compressed position.

4. The incontinence device of claim 1, wherein the distal body member is S-shaped.

5. The incontinence device of claim 1, wherein the incontinence device is symmetrical such that placement of the upper or lower surface of the distal body member in direct contact with a posterior wall of the vaginal canal during deployment will not cause any harm to the human user.

6. The incontinence device of claim 1, wherein the proximal pressure member varies in thickness as the proximal pressure member extends from the distal body member to the uncoupled second end of the pressure member.

7. The incontinence device of claim 6, wherein the thickness of the pressure member tapers as the pressure member extends away from the distal body member.

8. An incontinence device insertable into and removable from a vaginal canal of a human user to apply pressure upon a urethra comprising:

a distal body member including a central core having a first end and a second end, a first arcuate arm including a first end and second end, and a second arcuate arm including a first end and a second end, the first end of the first arcuate arm is coupled to a first side of the central core and the first end of the second arcuate arm is coupled on a second opposite side of the central core, the first and second arcuate arms flex inward toward the central core into a first compressed position during insertion and expand outward away from the central core into a second in use position to fill middle and superior thirds of the vaginal canal in order to retain the incontinence device in the vaginal canal, wherein the first arcuate arm extends from an end of the central core where the first end of the first arcuate arm is coupled to the central core to form a loop with the second end of the first arcuate arm located adjacent to an opposite end of the central core and the second arcuate arm extends from an end of the central core where the first end of the second arcuate arm is coupled to the central core to form a loop with the second end of the second arcuate arm located adjacent to an opposite end of the central core; and a proximal pressure member extending from the central core of the distal body member for resilient movement relative to the distal body member;

wherein the pressure member applies pressure to support the urethra for controlling incontinence.

9. The incontinence device of claim 8, further including a cord attached to the first and second arcuate arms used to remove the incontinence device from the vaginal canal.

10. The incontinence device of claim 8, wherein the distal body member is S-shaped.

11. The incontinence device of claim 8, wherein the proximal pressure member varies in thickness as the proximal pressure member extends from the distal body member to the uncoupled second end of the pressure member.

12. The incontinence device of claim 11, wherein the uncoupled second member of the proximal pressure member further includes protrusions on opposite sides thereof.

13. The incontinence device of claim 11, wherein the thickness of the proximal pressure member tapers as the proximal pressure member extends away from the distal body member.

14. An incontinence device insertable into and removable from a vaginal canal of a human user to apply pressure upon a urethra comprising:

a distal body member including a central core having a first end and a second end, a first arcuate arm including a first end and second end, and a second arcuate arm including a first end and a second end, the first end of the first arcuate arm is coupled to a first side of the central core and the first end of the second arcuate arm is coupled on a second opposite side of the central core, the first and second arcuate arms flex inward toward the central core into a first compressed position during insertion and expand outward away from the central core into a second in use position to fill middle and superior thirds of the vaginal canal in order to retain the incontinence device in the vaginal canal, wherein the first arcuate arm extends from an end of the central core where the first end of the first arcuate arm is coupled to the central core to form a loop with the second end of the first arcuate arm located adjacent to an opposite end of the central core and the second arcuate arm extends from an end of the central core where the first end of the second arcuate arm is coupled to the central core to form a loop with the second end of the second arcuate arm located adjacent to an opposite end of the central core; and a proximal pressure member extending from the distal body member for resilient movement relative to the distal body member, the proximal pressure member includes a first end coupled to the second end of the central core and an uncoupled second end, a junction of the central core and the proximal pressure member defines a flexion point from which the proximal pressure member flexes allowing for relative movement between the distal body member and the proximal pressure member, the proximal pressure member also includes an upper surface, a lower surface, and first and second lateral side walls extending between the upper and lower surfaces, wherein a first elongated protrusion is provided along the upper surface at the second end of the proximal pressure member and a second elongated protrusion is provided along the lower surface at the second end of the proximal pressure member;

wherein the pressure member applies pressure to support the urethra for controlling incontinence.

15. The incontinence device of claim 14, further including a cord attached to the first and second arcuate arms used to remove the incontinence device from the vaginal canal.

16. The incontinence device of claim 14, wherein the distal body member is S-shaped.

17. The incontinence device of claim 14, wherein the proximal pressure member varies in thickness as the proximal pressure member extends from the distal body member to the uncoupled second end of the proximal pressure member.

18. The incontinence device of claim 17, wherein the thickness of the proximal pressure member tapers as the proximal pressure member extends away from the distal body member.

* * * * *